US006455514B2

(12) United States Patent
Du Mesnil et al.

(10) Patent No.: US 6,455,514 B2
(45) Date of Patent: *Sep. 24, 2002

(54) PROCESS FOR TREATING LAMENESS BY ADMINISTRATION OF A BISPHOSPHONIC ACID DERIVATIVE

(75) Inventors: Philippe Du Mesnil, Bordeaux; Thierry Bardon, Bouliac; Dominique Thibaud, Bordeaux, all of (FR)

(73) Assignee: Ceva Sante Animale, Libourne (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/192,184

(22) Filed: Nov. 16, 1998

(30) Foreign Application Priority Data

Oct. 2, 1998 (FR) ............................................. 98 12388

(51) Int. Cl.⁷ ............................................. A01N 57/00
(52) U.S. Cl. ...................................................... 514/108
(58) Field of Search ........................................ 514/108

(56) References Cited

U.S. PATENT DOCUMENTS 4,234,645 A * 11/1980 Gunther et al. ............. 424/204
5,270,365 A * 12/1993 Gertz et al. ................. 514/108

FOREIGN PATENT DOCUMENTS

WO      WO97/12619      4/1997

OTHER PUBLICATIONS

J.D. Lillich, DVM et al., "Biochemical, Histochemical, and Immunohistochemical Characterization of Distal Tibial Osteochondrosis in Horses", *AJVR*, vol. 58, No. 1, Jan. 1997, pp. 89–98.

L.B. Jeffcott, "Osteochondrosis in the Horse–Searching for the Key to Pathogenesis", *Equine vet.J.*, (1991) 23 (5), pp. 331–338.

Mark B. Hurtig et al., "Pathogenesis of Equine Osteochondrosis", Section IV, Chapter 20, *Other Joint Entities*, pp. 335–359 (1990).

C. Wayne McIlwraith, "General Pathobiology of the Joint and Response to Injury", Chapter 3, pp. 40–71. (1991).

C. Wayne McIlwraith, "Current Concepts in Equine Degenerative Joint Disease", *The American Veterinary Medical Association Journal*, vol. 180, No. 3, Feb. 1, 1982, pp. 239–250.

Lepage et al., L'emploi d'un bisphosphonate (APD) dans la prévention des exostoses chez le poney Shetland. Etude Préliminaire, *Ann. Méd. Vét.*, 1988, 132, 391–399.

* cited by examiner

*Primary Examiner*—Theodore J. Criares
(74) *Attorney, Agent, or Firm*—Jacobson Holman, PLLC

(57) ABSTRACT

The invention relates to a process for treating lameness with an osseous, articular or osteoarticular component, comprising the administration, to a human or to an animal not suffering from arthritis or from fractures, of an effective amount of a bisphosphonic acid derivative of formula:

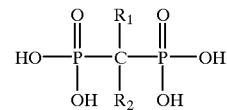

in which:

$R_1$ represents a hydrogen atom, a halogen atom, a hydroxyl, an amino, a mono($C_1$–$C_4$)alkylamino or a di($C_1$–$C_4$)alkylamino;

$R_2$ represents a halogen atom, a linear alkyl comprising from 1 to 5 carbon atoms which is unsubstituted or substituted with a group chosen from a chlorine atom, a hydroxyl, an amino, a mono($C_1$–$C_4$)alkylamino or a di($C_1$–$C_4$)alkylamino; a ($C_3$–$C_7$) cycloalkylamino, or $R_2$ represents a phenoxy, a phenyl, a thiol, a phenylthio, a chlorophenylthio, a pyridyl, a pyridyl-methyl, a 1-pyridyl-1-hydroxymethyl, an imidazolyl-methyl or a 4-thiomorpholinyl, of one of its pharmaceutically acceptable salts or of one of its hydrates.

7 Claims, No Drawings

PROCESS FOR TREATING LAMENESS BY ADMINISTRATION OF A BISPHOSPHONIC ACID DERIVATIVE

The present invention relates to a process for treating lameness with an osseous, articular or osteoarticular component in human or veterinary medicine, comprising the administration of a bisphosphonic acid derivative.

The term lameness is understood to refer to irregular gait caused by the perception of a pain by partially or fully bearing weight on one or more limbs during the functioning of limbs prompted into motion.

Lameness can manifest itself clinically in an intermittent or continuous manner for several days, several weeks or several months.

Lameness results more specifically from the appearance of painful lesions on the bone structure, the cartilages, the ligaments, the synovial membrane or the connective tissue or from an anomaly of local vascularization. Thus, lameness is generally associated with one or more of the following components:

an osseous component which is the result of a change in the bone architecture and/or in the bone growth cartilages at the site of the lameness, such as, for example, losses of bone substance, the formation of cysts, deformation of the bone or excessive thickening of the growth cartilages;

an articular component which is the result of a change in the structure of the articular cartilages, such as, for example, erosions of the cartilaginous surfaces and/or a change in the synovial membrane and/or a change in the articular ligaments;

a muscular component which is the result of a change in muscle development, such as, for example, a muscular atrophy; and a vascular component which is the result of a change in local vascularization, such as, for example, a reduction in vascularization of the injured region.

The invention is directed towards providing a process for treating lameness with an osseous component and/or with an articular component which appear in a person or an animal not suffering from fractures or arthritis. Hereinbelow, lameness is referred to by the expression lameness with an osseous, articular or osteoarticular component. It should be understood, however, that the osseous, articular or osteoarticular component can be present alone or combined with a muscular component and/or with a vascular component.

Lameness with an osseous, articular or osteoarticular component appear in particular during osteoarthrosis, osteochondrosis, navicular disease or enthesopathy of the bony insertions of the tendons, of the ligaments or of the aponeurosis.

Among the factors which can bring about lameness with an osseous, articular or osteoarticular component, mention may be made of constant and/or intense mechanical stresses on the locomotor apparatus. In the case of a person or animal unprepared for physical exercise, the intensity of the mechanical stress capable of bringing about lameness may be relatively low.

In contrast, in the case of a person or animal prepared for physical exercise, lameness will appear when subjected to a mechanical stress whose force or repetitive nature exceeds the resistance capacities of the limbs. Certain animal species are more particularly inclined to develop lameness with an osseous, articular and/or osteoarticular component. This is especially the case for equidae animals.

In point of fact, in horses, the locomotor apparatus is stressed more frequently than it is in other animal species, either during sporting competitions or when the horse is used by people as a mount. In this animal species, lameness represents one of the main clinical conditions requiring veterinary consultation. Their clinical description is well known; a fairly exhaustive review on this subject is presented in the book "Les boiteries du cheval" [Lameness in horses] edited by O. R. Adams (published by Maloine, 1990). Lameness with an osseous, articular or osteoarticular component are the most common; descriptions have especially been given in the art for navicular disease or horse podotrochlear syndrome, bone spavin or osteoarthrosis of the distal stage of the tarsus in horses, horse osteochondrosis and enthesopathy of the bony insertions of the tendons, of the ligaments or of the aponeurosis in horses.

Thus, the invention relates to a process for treating lameness with an osseous, articular or osteoarticular component, comprising the administration, to a person or to an animal (for example a horse) not suffering from fractures or from arthritis, of a bisphosphonic acid derivative.

The bisphosphonic acid derivatives which can be used in the context of the invention have the general formula:

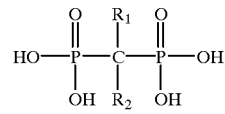

in which:

$R_1$ represents a hydrogen atom, a halogen atom, a hydroxyl, an amino, a mono($C_1$-$C_4$)alkylamino or a di($C_1$-$C_4$)alkylamino;

$R_2$ represents a halogen atom, a linear alkyl comprising from 1 to 5 carbon atoms which is unsubstituted or substituted with a group chosen from a chlorine atom, a hydroxyl, an amino, a mono($C_1$-$C_4$)alkylamino, a di($C_1$-$C_4$)alkylamino; a ($C_3$-$C_7$)cycloalkylamino, or $R_2$ represents a phenoxy, a phenyl, a thiol, a phenylthio, a chlorophenylthio, a pyridyl, a pyridyl-methyl, a 1-pyridyl-1-hydroxymethyl, an imidazolylmethyl or a 4-thiomorpholinyl.

The salts of these compounds with pharmaceutically acceptable inorganic or organic acids or bases can also be used in the context of the invention. Examples of salts with acids are hydrochloride, hydrobromide, sulphate, acetate, hydrogensulphate, dihydrogenphosphate, methanesulphonate, methylsulphate, maleate, fumarate, sulphonate, 2-naphthalenesulphonate, glycolate, gluconate, citrate, isethionate, benzoate, salicylate, ascorbate, tartrate, succinate, lactate, glutarate, toluenesulphonate and ascorbate. As examples of salts with inorganic or organic bases, mention may be made of ammonium salts or alkali metal salts such as, for example, sodium salts.

The hydrates of these compounds can similarly be used according to the invention.

These compounds are described in particular in EP 623, 347.

Among these bisphosphonic acid derivatives, mention may be made in particular of the following compounds:

1-hydroxyethylidenebisphosphonic acid, whose international nonproprietary name is etidronic acid, and its sodium salts;

2-pyrid-2-ylethylidenebisphosphonic acid, whose international nonproprietary name is piridronic acid, and its sodium salts;

dichloromethylenebisphosphonic acid, whose international nonproprietary name is clodronic acid, and its sodium salts;

3-amino-1-hydroxypropylidenebisphosphonic acid, whose international nonproprietary name is pamidronic acid, and its sodium salts;

4-amino-1-hydroxybutylidenebisphosphonic acid, whose international nonproprietary name is alendronic acid, and its sodium salts;

6-amino-1-hydroxyhexylidenebisphosphonic acid and its salts;

phenoxymethylenebisphosphonic acid and its salts;

thiomorpholinomethylenebisphosphonic acid and its salts;

4-chlorophenylthiomethylenebisphosphonic acid, whose international nonproprietary name is tiludronic acid, and its pharmaceutically acceptable salts, in particular the disodium salt;

1-hydroxy-2-(3-pyridyl)ethylidenebisphosphonic acid, whose international nonproprietary name is risedronic acid, and its sodium salts;

1-hydroxy-2-(2-imidazolyl)ethyl-1,1-bisphosphonic acid and its salts;

(cycloheptylamino)methylenebisphosphonic acid and its salts;

2-hydroxyethylidene-2-(3-pyridyl)-1,1-bis-phosphonic acid and its sodium salts.

According to the present invention, the administration of tiludronic acid and of its pharmaceutically acceptable salts, in particular the disodium salt, or of its hydrates is particularly preferred.

Bisphosphonic acid derivatives are known to inhibit bone resorption and to decrease the activity of osteoclasts, as is found in particular in the following articles:

"Diphosphonates inhibit hydroxyapatite dissolution in vitro and bone resorption in tissue culture and in vivo", Fleisch H., Russell R., Francis M., Science, 1969, 165, 1262–1264

"Two modes of action of bisphosphonates on osteoclastic resorption of mineralized matrix", Boonekamp P. M., Van Der Wee-Pals L. J. A., Van Wijk-Lennep, Thesing C. W., Bijvoet O. L. M., Bone Miner., 1986, 1, 27–39

"Dichloromethylene bisphosphonate ($Cl_2MBP$) inhibits bone resorption through injury to osteoclasts that resorb CIMBP coated bone", Flanaghan A. M., Chambers T. J., Bone Miner., 1989, 6, 33.

Many bisphosphonic acid derivatives are in development or are already marketed in human medicine in the treatment of bone complaints. A review of the therapeutic uses of these derivatives is presented in the book "Bisphosphonate on bones" edited by Bijvoet O. L. M., Fleisch H. A., Canfield R. E. and Russell R. G. G. (Elsevier Science BV, 1995). The main uses concern the treatment of bone complaints such as Paget's disease or osteoporosis. The other uses usually described are directed towards the treatment of malignant hypercalcaemia, bone tumours or bone metastasis. It has also been possible to demonstrate the anti-inflammatory activity of certain bisphosphonic acid derivatives in a model of arthritis in rats, induced by injection of mycobacterium.

However, the authors are unaware of any studies demonstrating the anti-inflammatory activity of these bisphosphonic acid derivatives in pathologies other than arthritis or more generally in other species (and for example in man). More recently, the value of certain bisphosphonic acid derivatives in improving the repair of fractures has been described. Reference will be made in particular to EP 600,834 or U.S. Pat. No. 5,488,041.

In another field, the use of bisphosphonic acid derivatives is also described in the diagnosis of certain bone complaints by scintigraphy. An example of such a use is reported by Keegan K. G., Wilson D. A., Lattimer C. L., Twardock A. R., Ellersieck M. R. (Am. J. Vet. Res., 1996, 57, 415–421) in the scintigraphic evaluation of $^{99m}$Tc-methylene diphosphonate labelling of the navicular region in horses with lameness localized on the foot. However no mention is made of the clinical benefit provided by binding the bisphosphonic acid derivative in the bones of the palmar region.

The medical treatments most usually prescribed for lameness are directed towards pain relief; this is the case, for example, for treatments with non-steroidal anti-inflammatory medicines. However, these treatments are unsatisfactory since they do not treat the injuries which are the cause of the inflammation. Their efficacy is moreover limited to the period of administration, since the beneficial effects of the anti-inflammatories disappear as soon as treatment has ended. Rest is also often recommended to allow the region of the locomotor apparatus, which is the cause of lameness, to return to a normal state. More specifically, in horses, the use of orthopaedic shoes is recommended. Even more particularly, in this animal species, the use of compounds which modify vascularization in the navicular region is recommended in the treatment of navicular disease; it is for these conditions that isoxsuprine, a vasodilator, is prescribed by Gabriel A., Caudron I., Serteyn D., Collin B. in "Syndrome naviculaire: anatomie, étiopathogénie, diagnostic, traitement" [Navicular syndrome: anatomy, aetiopathology, diagnosis and treatment], Ann. Med. Vet., 1994, 138, 309–330).

Surprisingly, it has been found that bisphosphonic acid derivatives are useful in the treatment of lameness with an osseous, articular or osteoarticular component. It has been shown, entirely unexpectedly, that the use of these derivatives allows a significant and long-lasting improvement in the clinical signs of lameness, or even curing of lameness, even beyond the treatment period, and without any increase in bone density being detectable by radiological examination.

Thus, the beneficial effects observed are not thought to be linked to the bone resorption-inhibiting activity of the bisphosphonic acid derivatives.

Such medicines can be used in human medicine and in veterinary medicine.

They can be administered via various routes of administration, for example parenterally, orally, rectally, intra-articularly, cutaneously, transcutaneously or transdermally.

The mode of administration of such medicines is determined depending on the species treated, age, weight and the severity of the pathology.

The administration rhythm can consist of a single administration or repeated administrations. In the case of repeated administrations, the treatment can be administered continuously or intermittently. When a continuous treatment is chosen, the preferred administration rhythm may be from a single daily administration to 3 daily administrations over a period which can range from a few days to a few months. When an intermittent treatment is chosen, one of the following administration rhythms may be adopted: an administration every 2 or 3 days or a weekly, bimonthly or monthly administration over periods which can range from a few weeks to a few months.

The concentration of the medicine, in terms of bisphosphonic acid derivative, depends on the activity and on the duration of action of this derivative, the mode of administration, the age, the weight, the sex, the importance of the desired effect, the intended species or, for certain animal species, the race.

For liquid preparations for parenteral or oral use, the concentration of the medicine, in terms of bisphosphonic acid derivative, can be between 0.001% and 900 % as a weight/volume ratio. For preparations intended for the oral route, it can be between 0.001 mg and 10 g per dosage unit.

The medicine can also be in the form of an implant.

The doses during each administration of the medicines prepared according to the present invention, expressed relative to the body weight, can range between 0.001 mg/kg and 100 mg/kg.

For example, doses of from 0.01 mg/kg/week to 1 mg/kg/week of tiludronic acid or of one of its salts may be administered intravenously to horses.

For an oral administration, the pharmaceutical composition which can be used according to the invention may be in the form of a tablet, a gelatin capsule, a powder, a granule, drops or any other form which can be administered orally.

The composition which can be used according to the invention may also contain ingredients usually used in pharmacy for the preparation of oral forms. Thus, the said composition can contain a disintegration agent, a flow agent, a lubricant and any excipient of suitable mass.

Lactose, cellulose or starches can be used as mass excipient. Stearic acid, magnesium stearate, L-leucine or, for example, glyceryl tribehenate can be used as lubricant. Sodium carboxymethylstarch, crosslinked sodium carboxymethylcellulose or, for example, crosslinked polyvinylpyrrolidone can be used as disintegration agent. Pure silica or colloidal silicon dioxide can be used as flow agent.

The present invention also relates to rapidly dissolving oral forms and to effervescent oral forms obtained by adding an effervescent couple to the composition according to the invention. Tartaric acid and sodium bicarbonate or citric acid and sodium bicarbonate can be used as effervescent couple.

The invention also relates to the use of rapidly dissolving tablets, effervescent tablets and tablets covered with a coating. A composition containing sodium lauryl sulphate according to European patent EP 336,851 is particularly suitable.

For rectal administration, use is made of suppositories which are prepared with binders that melt at rectal temperature, for example cocoa butter or polyethylene glycols.

The preparations for injection are prepared by mixing one or more bisphosphonic acid derivatives with a pH regulator, a buffer agent, a suspension agent, a solubilization agent, a stabilizer, a tonicity agent and/or a preserving agent, and by converting the mixture into an intravenous, subcutaneous or intramuscular injection, according to a standard process. Where appropriate, the preparations for injection can be lyophilized according to a standard process.

Examples of suspension agents include methylcellulose, polysorbate-80, hydroxyethylcellulose, acacia, powdered gum tragacanth, sodium carboxymethylcellulose and polyethoxylated sorbitan monolaurate.

Examples of solubilizing agents include castor oil solidified with polyoxyethylene, polysorbate-80, nicotinamide, polyethoxylated sorbitan monolaurate, macrogol and the ethyl ester of castor oil fatty acid.

In addition, Examples of the stabilizer includes sodium sulphite, sodium metasulphite and ether, while examples of the preserving agent includes methyl p-hydroxybenzoate, ethyl p-hydroxybenzoate, sorbic acid, phenol, cresol and chlorocresol.

An example of a tonicity agent is mannitol.

During the preparation of the solutions or suspensions for injection, it is desirable to take care to ensure that these are isotonic with the blood.

EXAMPLE 1

A clinical study was carried out to evaluate the effects of a treatment with disodium tiludronate on horses which develop lameness during navicular disease (also known as podotrochlear syndrome).

The study was carried out on 24 horses, the diagnosis of the navicular disease causing lameness being based on the following criteria:

local signs in the palmar region: heat, swelling, pain functional signs of limping graded on a scale from 0 (no sign of limping) to 4 (trouble in bearing weight when at rest and/or in motion and difficulty in moving around)

a functional test of locomotion after flexing the palmar region, also assessed on a scale from 0 (locomotion not changed by flexure) to 4 (start of suppression of bearing weight)

a radiological examination to assess radiological signs in the palmar region qualitatively.

To be included, the animal had to show no signs or lesions of septic arthritis, or any fractures of the bones in the palmar region. Also, it needed to have not received an injection for anti-inflammatory treatment in the joints of the palmar region.

The wearing of an orthopaedic shoe was not contraindicated since most of the animals had been laming for several weeks and were already wearing a shoe of this type.

All the animals received, as a single treatment, disodium tiludronate in the form of an injectable solution administered intravenously at a dose of 0.1 mg/kg, at a weekly administration rate for 6 to 10 weeks. The first day of treatment corresponds to D0.

To assess the effects of the treatment, the animals were reviewed 1 month after D0 (M1), 2 months after D0 (M2) and 6 months after D0 (M6). The effects of the treatment were assessed with regard to:

the local signs, the functional signs and the test of locomotion after flexure as defined during inclusion of the animal into the test a radiological examination to assess the change in the radiological signs an assessment of the resumption of the animal's sporting activity.

Taking all these criteria into account allows the horse to be placed in one of the following categories after the 3 control examinations at M1, M2 and M6:

"very favourable" category: absence of local signs, grade 0 for the functional test and signs; the animal resumed activity comparable to that in which it was engaged before limping "favourable" category: the local signs are very much attenuated, the functional signs have been improved by 1 or 2 degrees, the horse is ready to resume physical activity comparable to that in which it was engaged before limping "average" category: persistence of local signs, functional signs improved by 1 degree; persistence of a locomotor difficulty preventing the animal from resuming normal physical activity "mediocre" category: persistence of the local signs, no improvement in the functional signs "poor" category: no improvement in the local or functional signs, or even worsening of the local signs and of the functional signs.

The table below summarizes the effects of the treatment (expressed as a percentage of animals present in each category):

| Category | Examination at M1 | Examination at M2 | Examination at M6 |
|---|---|---|---|
| Very favourable | 8% | 26% | 18% |
| Favourable | 46% | 43% | 46% |
| Average | 38% | 26% | 27% |
| Mediocre | 4% | 5% | 9% |
| Poor | 4% | 0% | 0% |

These results demonstrate the beneficial effects of administration of the bisphosphonic acid derivative, by revealing a change in kinetics of lameness. The benefit of the treatment is optimal 2 months after administration of the treatment is started. The treatment leads to a complete recovery for a quarter of the animals at the end of its administration. The benefit of the treatment is maintained in an entirely satisfactory manner beyond the treatment period.

Radiological examination did not reveal any change in kinetics of the pathological radiological signs in the palmar region.

EXAMPLE 2

A clinical study was carried out in order to evaluate the effects of a treatment with disodium tiludronate on horses which develop lameness during bone spavin (which is osteoarthrosis of the distal stage of the tarsus).

The test procedure and the clinical monitoring of the animals were the same as those described in Example 1, except that the local, functional and radio-logical signs were assessed in the region of the hock.

5 horses were included in this test.

The results obtained were as follows (expressed as a percentage of animals present in each category):

| Category | Examination at M1 | Examination at M2 | Examination at M6 |
|---|---|---|---|
| Very favourable | 0% | 40% | 40% |
| Favourable | 40% | 60% | 20% |
| Average | 60% | 0% | 20% |
| Mediocre | 0% | 0% | 0% |
| Poor | 0% | 0% | 20% |

The change in lameness induced by bone spavin is favourable to very favourable in most of the animals after treatment. The persistence of the beneficial effects is also very satisfactory.

EXAMPLE 3

A clinical study was carried out to evaluate the effects of a treatment with disodium tiludronate on horses which develop lameness associated with bone lesions in the form of sub-chondral cysts during osteochondrosis.

The test procedure and the clinical monitoring of the animals were the same as those described in Example 1, except that the local, functional and radio-logical signs were evaluated in the joints affected by osteochondrosis.

5 horses were included in this test.

The results obtained were as follows (expressed as a percentage of animals present in each category):

| Category | Examination at M1 | Examination at M2 | Examination at M6 |
|---|---|---|---|
| Very favourable | 40% | 20% | 60% |
| Favourable | 0% | 40% | 0% |
| Average | 40% | 20% | 0% |
| Mediocre | 0% | 0% | 40% |
| Poor | 20% | 20% | 0% |

These results demonstrate the clinical benefit afforded by administration of the bisphosphonic acid derivative on the treatment of lameness associated with bone lesions during osteochondrosis.

EXAMPLE 4

A clinical study was carried out to evaluate the effects of a treatment with disodium tiludronate on horses which develop lameness during enthesopathy of the insertion of the tendons and the ligaments.

The test procedure and the clinical monitoring of the animals were the same as those described in Example 1, except that the local, functional and radio-logical signs were evaluated in the region of the tendon or ligament insertions at the source of lameness.

6 horses were included in this test.

The results obtained were as follows (expressed as a percentage of animals present in each category):

| Category | Examination at M1 | Examination at M2 | Examination at M6 |
|---|---|---|---|
| Very favourable | 0% | 0% | 40% |
| Favourable | 50% | 67% | 40% |
| Average | 33% | 33% | 0% |
| Mediocre | 17% | 0% | 20% |
| Poor | 0% | 0% | 0% |

These results demonstrate the clinical benefit afforded by administration of the bisphosphonic acid derivative on the treatment of lameness caused by insertion enthesopathies.

What is claimed is:

1. Process for treating lameness that appears during osteochondrosis comprising the administration, to a human or to an animal not suffering from arthritis or from fractures, of an effective amount of a bisphosphonic acid derivative of formula:

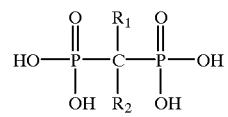

in which:
  $R_1$ represents a hydrogen atom, a halogen atom, a hydroxyl, an amino, a mono($C_1$–$C_4$)alkylamino or a di($C_1$–$C_4$)alkylamino;
  $R_2$ represents a halogen atom, a linear alkyl comprising 1 to 5 carbon atoms which is unsubstituted or substituted with a chlorine atom, a hydroxyl, an amino, a mono ($C_1$–$C_4$)alkylamino, or a di($C_1$–$C_4$)alkylamino; a ($C_3$–$C_7$)cycloalkylamino,
  or $R_2$ represents a phenoxy, a phenyl, a thiol, a phenylthio, a chlorophenylthio, a pyridyl, a pyridylmethyl, a 1-pyridyl-1-hydroxymethyl, an imidazolylmethyl, or a 4- thiomorpholinyl, or one of its pharmaceutically acceptable salts or one of its hydrates.

2. Process according to claim 1, for treating a horse.

3. Process according to claim 1, comprising the administration of 0.001 mg/kg to 100 mg/kg of body weight of the bisphosphonic acid derivative.

4. Process according to claim 1, for treating limps in horses, comprising the intravenous administration of 0.01 mg/kg body weight/week to 1 mg/kg body weight/week of tiludronic acid or one of its pharmaceutically acceptable salts.

5. Process according to claim 1, comprising the oral or parenteral administration or the administration in the form of an implant of the bisphosphonic acid derivative.

6. Process according to claim 1, in which the bisphosphonic acid derivative is selected from the group consisting of:

1-hydroxyethylidenebisphosphonic acid and its sodium salts;

2-pyrid-2-ylethylidenebisphosphonic acid and its sodium salts;

dichloromethylenebisphosphonic acid and its sodium salts;

3-amino-1-hydroxypropylidenebisphosphonic acid and its sodium salts;

4-amino-1-hydroxybutylidenebisphosphonic acid and its sodium salts;

6-amino-1-hydroxyhexylidenebisphosphonic acid and its salts;

phenoxymethylenebisphosphonic acid and its salts;

thiomorpholinomethylenebisphosphonic acid and its salts;

4-chlorophenylthiomethylenebisphosphonic acid and its salts;

1-hydroxy-2-(3-pyridyl)ethylidenebisphosphonic acid and its salts;

1-hydroxy-2-(2-imidazoly)ethyl-1,1-bisphosphonic acid and its salts;

(cycloheptylamino)methylenebisphosphonic acid and its salts; and 2-hydroxyethylidene-2-(3-pyridyl)-1,1-bisphosphonic acid and its sodium salts.

7. Process according to claim 1, in which the bisphosphonic acid derivative is 4-chlorophenylthiomethylenebisphosphonic acid.

* * * * *